United States Patent [19]
Tsuboi et al.

[11] Patent Number: 5,507,862
[45] Date of Patent: Apr. 16, 1996

[54] ANTI-FOULING COMPOSITIONS OR FOULING CONTROL OF HARMFUL AQUATIC ORGANISMS

[75] Inventors: Makoto Tsuboi; Shuhei Yuki, both of Hiroshima; Kenji Arai, Toyonaka; Tomohiro Teramae, Takarazuka; Masato Mizutani, Nishinomiya, all of Japan

[73] Assignees: Sumitomo Chemical Company, Limited, Osaka; Chugoku Marine Paints, Ltd., Hiroshima, both of Japan

[21] Appl. No.: 305,922

[22] Filed: Sep. 16, 1994

[30] Foreign Application Priority Data

Sep. 17, 1993 [JP] Japan .................................. 5-231373
Dec. 27, 1993 [JP] Japan .................................. 5-333792

[51] Int. Cl.$^6$ ............................ C09D 5/16; A01N 31/00
[52] U.S. Cl. ...................... 106/18.33; 424/630; 424/638; 514/372; 514/373; 523/122
[58] Field of Search ...................... 106/18.33; 424/78.09, 424/630, 632, 634, 638; 523/122; 514/372, 373; 427/385.5

[56] References Cited

U.S. PATENT DOCUMENTS

| | | |
|---|---|---|
| 3,012,039 | 12/1961 | Morley . |
| 4,243,403 | 1/1981 | Lewis et al. .................. 106/18.33 |
| 4,822,511 | 4/1989 | Law ................................ 106/18.33 |
| 5,108,500 | 4/1992 | Mattox .......................... 106/18.33 |
| 5,125,967 | 6/1992 | Morpeth et al. .............. 106/18.33 |
| 5,188,663 | 2/1993 | Ikari et al. .................... 106/18.33 |
| 5,364,874 | 11/1994 | Morpeth ...................... 106/18.33 |

FOREIGN PATENT DOCUMENTS

| | | | |
|---|---|---|---|
| 2439619 | 2/1975 | Germany ..................... 106/18.33 |
| 51-113 | 1/1976 | Japan . | |

*Primary Examiner*—Anthony Green
*Attorney, Agent, or Firm*—Birch, Stewart, Kolasch & Birch

[57] ABSTRACT

There are disclosed a controlling agent and an antifouling composition against harmful aquatic organisms, which include a particular N-phenylbenzoisothiazolone derivative of the formula:

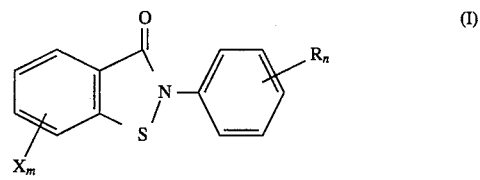

wherein R's are the same or different and are independently halogen, alkyl or alkoxy; n is an integer of 0 to 5; X's are the same or different and are independently halogen, nitro, alkyl or alkoxy; and m is an integer of 0 to 4; with the proviso that when the R's are all alkyl or all alkoxy, n is an integer of 1 to 3, and when all of the R's are different, n is an integer of 2 or 3. Also disclosed is a method for preventing or inhibiting the adhesion of harmful aquatic organisms to water-exposed articles, which includes applying the antifouling composition to the water-exposed articles.

27 Claims, No Drawings

ANTI-FOULING COMPOSITIONS OR FOULING CONTROL OF HARMFUL AQUATIC ORGANISMS

FIELD OF THE INVENTION

The present invention relates to fouling control of harmful aquatic organisms which adhere to various water-exposed articles. The term "water-exposed articles" is used herein to cover marine vessels, buoys, littoral industrial plants, inlet channels for cooling water in thermal or nuclear power stations, drilling rigs for submarine oil fields, harbor facilities and sea pollution preventive bands for ocean civil engineering works, and the like.

BACKGROUND OF THE INVENTION

As there can be found many kinds of animals and plants living in the sea, various organisms may often adhere to water-exposed articles and have adverse effects thereon. The adhesion of such harmful aquatic organisms will cause a decrease in the service speed and an increase in the fuel consumption of marine vessels, and a decrease in the carrying capacity of inlet channels of cooling water.

To control these adhering organisms, various antifouling agents such as cuprous oxide have hitherto been used; however, their efficacy is not sufficient.

SUMMARY OF THE INVENTION

Under these circumstances, the present inventors have intensively studied to find methods of more effectively preventing and inhibiting various organisms adhering to water-exposed articles. As a result, they found that particular N-phenylbenzoisothiazolone derivatives have an effect on the prevention and inhibition of adhesion of harmful aquatic organisms, for example, harmful aquatic animals such as barnacles and sea mussels; harmful aquatic plants such as algae and diatoms; and harmful aquatic objects such as slime, thereby completing the present invention.

Thus, the present invention provides a controlling agent and an antifouling coating against harmful aquatic organisms, which comprise an N-phenylbenzoisothiazolone derivative of the formula:

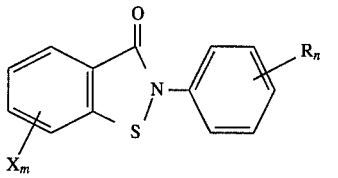

(I)

wherein R's are the same or different and are independently halogen, alkyl or alkoxy; n is an integer of 0 to 5; X's are the same or different and are independently halogen, nitro, alkyl or alkoxy; and m is an integer of 0 to 4; with the proviso that when R's are all alkyl or all alkoxy, n is an integer of 1 to 3, and when all of the R's are different, n is an integer of 2 or 3.

The present invention also provides a method for preventing and inhibiting the adhesion of harmful aquatic organisms to water-exposed articles, which comprises applying the antifouling composition of the present invention to the water-exposed articles.

DETAILED DESCRIPTION OF THE INVENTION

The controlling agent and antifouling coating of the present invention contain an N-phenylbenzoisothiazolone derivative of the formula (I), which is hereinafter referred to as the compound (I), as an active ingredient. Compound (I) is disclosed in the U.S. Pat. No. 3,012,039 and a process of producing this compound is disclosed in the Japanese Patent Publication No. 51-113/1976.

As used herein, the term "halogen" refers to chlorine, fluorine, bromine or iodine. The term "alkyl" refers to $C_1$–$C_{10}$ alkyl such as methyl, ethyl, n-propyl, iso-propyl, n-butyl, isobutyl, tert-butyl, sec-butyl, tert-amyl, n-pentyl, n-hexyl and n-decyl. Preferred is $C_1$–$C_4$ alkyl. The term "alkoxy" refers to $C_1$–$C_{10}$ alkoxy such as methoxy, ethoxy, n-propoxy, isopropoxy, n-butoxy, isobutoxy, tert-butoxy, sec-butoxy, tert-amyl oxy, n-pentyloxy, n-hexyloxy and n-decyloxy. Preferred is $C_1$–$C_4$ alkoxy.

The compound (I) has an effect on the prevention and inhibition of harmful aquatic organisms adhering to water-exposed articles, and such an effect can be retained for a long period of time. Examples of the harmful aquatic organisms are aquatic animals such as barnacles (Balanomorpha), Serpula, polyzoans (Polyzoa), Ascidiacea, Hydrozoa and mollusks (Mollusca); aquatic plants such as Ulva, Enteromorpha, Ectocarpus and diatoms (Diatomaceae); and slime.

In case where the compound (I) is used for the purpose of preventing and inhibiting the adhesion and propagation of harmful aquatic organisms adhering to water-exposed articles, it may be applied in the form of a solution or emulsion. Preferably, it is applied in the form of a resin-containing composition. In particular, to water-exposed articles present in the sea, the antifouling composition of the present invention is applied.

The compound (I) can be made into an antifouling composition by ordinary formulation which is usually employed in the field of coatings. It is noted that the compound (I) has no adverse effect on the storage stability, such as viscosity increase and quality change.

The antifouling composition of the present invention contains the compound (I) in a mixture with a resin. Examples of the resin are vinyl chloride resins, vinyl chloride-vinyl acetate copolymers, vinyl chloride-vinyl isobutyl ether copolymers, chlorinated rubber resins, chlorinated polyethylene resins, chlorinated polypropylene resins, acrylic resins, styrene-butadiene copolymers, polyester resins, epoxy resins, phenolic resins, synthetic rubbers, silicone rubbers, silicone resins, petroleum resins, oil resins, rosin ester resins, rosin soap and rosin. Preferred are vinyl chloride resins, vinyl chloride-vinyl acetate copolymers, vinyl chloride-vinyl isobutyl ether copolymers, acrylic resins and styrene-butadiene copolymers.

The resin is mixed in an amount of 0.1% to 80% by weight, preferably 0.1% to 60% by weight, based on the total weight of the controlling agent or antifouling composition of the present invention.

The antifouling composition of the present invention may further contain various additives which are usually used in conventional compositions, for example, plasticizers such as chlorinated paraffin and trimetacresyl phosphate; color pigments such as red iron oxide and titanium dioxide; extender pigments such as zinc oxide and silica powder; and organic solvents such as xylene and methyl isobutyl ketone.

Preferably, a copper compound or a metallic copper is added to the control ling agent and antifouling composition of the present invention to obtain better controlling effects. Examples of the copper compound are cuprous oxide, copper rhodanide, oxine-copper, copper naphthenate, copper glycinate, cuprous chloride and cuprous carbonate. Preferred are cuprous oxide and copper rhodanide.

The controlling agent and antifouling composition of the present invention may further contain other conventional antifouling agents, if required. Examples of the antifouling agent are those which have been cited in the 2091th research meeting of the Japan Shipbuilding Research Association, such as zinc dimethyldithiocarbamate, 2-methylthio-4-t-butylamino-6-cyclopropylamino-s-triazine,2,4,5,6-tetrachloroisophthalonitrile, N,N-dimethyl-N'-(3,4-dichlorophenyl)urea, 4,5-dichloro-2-n-octyl-4-isothiazolin-3-one, N-(fluorodichloromethylthio)phthalimide, N,N-dimethyl-N'-phenyl-N'-(fluorodichloromethylthio)sulfamide, 2-pyridinethiol-1-oxide zinc salt, tetramethylthiuram disulfide, Cu-10% Ni solid solution alloy, N-(2,4,6-trichlorophenyl)-maleimide, 2,3,5,6-tetrachloro-4-(methylsulfonyl)pyridine, 3-iodo-2-propynylbutyl-carbamate, diiodomethyl-p-tolylsulfone, bisdimethyldithiocarbamoyl zinc ethylenebisdithiocarbamate and tetraphenylborane pyridine salt.

The compound (I) is mixed in an amount of 0.1 to 60% by weight, preferably 0.1 to 40% by weight, based on the total weight of the controlling agent or antifouling composition of the present invention. When the amount is less than 0.1% by weight, no controlling effect will be expected. When the amount is greater than 60% by weight, defects such as cracks and peeling will readily occur on the coating film formed from the antifouling composition.

In case where a copper compound is to be added to the controlling agent or antifouling composition of the present invention, the proportion of the copper compound to the compound (I) may vary case by case, but it is preferably in the range of 0.1 to 100 parts by weight to one part by weight of the compound (I). The total amount of compound (I) and copper compound is preferably 0.1% to 80% by weight, based on the total weight of the controlling agent or antifouling composition of the present invention. When the total amount is less than 0.1% by weight, no controlling effect will be expected. When the total amount is greater than 80% by weight, defects such as cracks and peeling will readily occur on the coating film formed from the antifouling composition, which makes it difficult to attain the desired antifouling effect.

The compound (I) can safely be applied as the antifouling composition of the present invention by means of a spray or the like because of its low irritant action.

Some typical examples of the compound (I) are shown in Table 1 below, which are to be construed as mere illustrations and not limitations of the preceding disclosure in any way whatsoever.

TABLE 1

| Compound No. | Compound name |
|---|---|
| (1) | N-phenylbenzoisothiazolone |
| (2) | N-(2-chlorophenyl)benzoisothiazolone |
| (3) | N-(3-chlorophenyl)benzoisothiazolone |
| (4) | N-(4-chlorophenyl)benzoisothiazolone |
| (5) | N-(4-bromophenyl)benzoisothiazolone |
| (6) | N-(2-fluorophenyl)benzoisothiazolone |
| (7) | N-(4-fluorophenyl)benzoisothiazolone |
| (8) | N-(2-methylphenyl)benzoisothiazolone |
| (9) | N-(3-methylphenyl)benzoisothiazolone |
| (10) | N-(4-methylphenyl)benzoisothiazolone |
| (11) | N-(2-ethylphenyl)benzoisothiazolone |
| (12) | N-(3-ethylphenyl)benzoisothiazolone |
| (13) | N-(4-ethylphenyl)benzoisothiazolone |
| (14) | N-(2-isopropylphenyl)benzoisothiazolone |
| (15) | N-(4-isopropylphenyl)benzoisothiazolone |

TABLE 1-continued

| Compound No. | Compound name |
|---|---|
| (16) | N-(2-methoxyphenyl)benzoisothiazolone |
| (17) | N-(3-methoxyphenyl)benzoisothiazolone |
| (18) | N-(4-methoxyphenyl)benzoisothiazolone |
| (19) | N-(4-ethoxyphenyl)benzoisothiazolone |
| (20) | N-(4-n-butoxyphenyl)benzoisothiazolone |
| (21) | N-(2,4-dichlorophenyl)benzoisothiazolone |
| (22) | N-(3,4-dichlorophenyl)benzoisothiazolone |
| (23) | N-(3,5-dichlorophenyl)benzoisothiazolone |
| (24) | N-(2,6-dichlorophenyl)benzoisothiazolone |
| (25) | N-(2,4,6-trichlorophenyl)benzoisothiazolone |
| (26) | N-(2,3,4,5,6-pentachlorophenyl)benzoisothiazolone |
| (27) | N-(2,4-difluorophenyl)benzoisothiazolone |
| (28) | N-(2,3,5,6-tetrafluorophenyl)benzoisothiazolone |
| (29) | N-(2,3,4,5,6-pentafluorophenyl)benzoisothiazolone |
| (30) | N-(2,4-dimethylphenyl)benzoisothiazolone |
| (31) | N-(3,4-dimethylphenyl)benzoisothiazolone |
| (32) | N-(3,5-dimethylphenyl)benzoisothiazolone |
| (33) | N-(2,6-dimethylphenyl)benzoisothiazolone |
| (34) | N-(2,4,6-trimethylphenyl)benzoisothiazolone |
| (35) | N-(3,4-dimethoxyphenyl)benzoisothiazolone |
| (36) | N-(3,5-dimethoxyphenyl)benzoisothiazolone |
| (37) | N-(3,4,5-trimethoxyphenyl)benzoisothiazolone |
| (38) | N-(2-chloro-4-methylphenyl)benzoisothiazolone |
| (39) | N-(2-fluoro-4-chlorophenyl)benzoisothiazolone |
| (40) | N-(2,6-dichloro-4-methylphenyl)benzoisothiazolone |
| (41) | N-(t-butylphenyl)benzoisothiazolone |
| (42) | N-(2,6-difluorophenyl)benzoisothiazolone |
| (43) | N-(4-iodophenyl)benzoisothiazolone |
| (44) | N-(4-chloro-2-methoxy-5-methylphenyl)benzoisothiazolone |
| (45) | N-(2,4-dichloro-3-methylphenyl)benzoisothiazolone |
| (46) | N-(4-ethoxy-3,5-dichlorophenyl)benzoisothiazolone |
| (47) | N-(2-chloro-4-methoxy-3-methylphenyl)benzoisothiazolone |
| (48) | N-(4-methoxy-3-chlorophenyl)benzoisothiazolone |
| (49) | N-(3-chloro-2,4-difluorophenyl)benzoisothiazolone |
| (50) | N-(3,4-diethoxyphenyl)benzoisothiazolone |
| (51) | 4-fluoro-N-phenylbenzoisothiazolone |
| (52) | 5-fluoro-N-phenylbenzoisothiazolone |
| (53) | 6-fluoro-N-phenylbenzoisothiazolone |
| (54) | 7-fluoro-N-phenylbenzoisothiazolone |
| (55) | 4-chloro-N-phenylbenzoisothiazolone |
| (56) | 5-chloro-N-phenylbenzoisothiazolone |
| (57) | 6-chloro-N-phenylbenzoisothiazolone |
| (58) | 7-chloro-N-phenylbenzoisothiazolone |
| (59) | 4-bromo-N-phenylbenzoisothiazolone |
| (60) | 5-bromo-N-phenylbenzoisothiazolone |
| (61) | 6-bromo-N-phenylbenzoisothiazolone |
| (62) | 7-bromo-N-phenylbenzoisothiazolone |
| (63) | 6-iodo-N-phenylbenzoisothiazolone |
| (64) | 4-methyl-N-phenylbenzoisothiazolone |
| (65) | 5-methyl-N-phenylbenzoisothiazolone |
| (66) | 6-methyl-N-phenylbenzoisothiazolone |
| (67) | 7-methyl-N-phenylbenzoisothiazolone |
| (68) | 6-ethyl-N-phenylbenzoisothiazolone |
| (69) | 7-propyl-N-phenylbenzoisothiazolone |
| (70) | 4-methoxy-N-phenylbenzoisothiazolone |
| (71) | 5-methoxy-N-phenylbenzoisothiazolone |
| (72) | 6-methoxy-N-phenylbenzoisothiazolone |
| (73) | 7-methoxy-N-phenylbenzoisothiazolone |
| (74) | 5-ethoxy-N-phenylbenzoisothiazolone |
| (75) | 7-isopropoxy-N-phenylbenzoisothiazolone |
| (76) | 4-nitro-N-phenylbenzoisothiazolone |
| (77) | 5-nitro-N-phenylbenzoisothiazolone |
| (78) | 6-nitro-N-phenylbenzoisothiazolone |
| (79) | 7-nitro-N-phenylbenzoisothiazolone |
| (80) | 5,7-dinitro-N-phenylbenzoisothiazolone |
| (81) | 4,5,6,7-tetrafluoro-N-phenylbenzoisothiazolone |
| (82) | 5-chloro-7-fluoro-N-phenylbenzoisothiazolone |
| (83) | 5-methoxy-7-chloro-N-phenylbenzoisothiazolone |
| (84) | 6-chloro-N-(4-chlorophenyl)benzoisothiazolone |
| (85) | 6-chloro-N-(2,3,4-trichlorophenyl)benzoisothiazolone |
| (86) | 5-methyl-N-(3-fluorophenyl)benzoisothiazolone |
| (87) | 6-methoxy-N-(4-chloro-2-methylphenyl)benzoisotiazolone |

TABLE 1-continued

| Compound No. | Compound name |
|---|---|
| (88) | 6-methoxy-N-(2,3,4,5,6-pentachlorophenyl)benzoisothiazolone |
| (89) | 7-methyl-N-(2-methyl-4-chloro-5-methoxyphenyl)-benzoisothiazolone |
| (90) | 5,7-dimethyl-N-(2-methyl-4-chloro-5-methoxyphenyl)-benzoisothiazolone |

The present invention will be further illustrated by the following examples, test examples and comparative examples, which are not to be construed to limit the scope thereof. Unless otherwise indicated, the term "part(s)" refers to part(s) by weight. Specific examples of the compound (I) are designated by the respective compound numbers shown in Table 1.

EXAMPLES 1–9 and Comparative Examples 1

To each of the compound (1), (4), (8), (16), (57), (67), (72) and (80) were added the ingredients as shown in Table 2. These mixtures were independently mixed and dispersed with a paint conditioner, which afforded compositions of Examples 1–9. In the same manner, a composition of Comparative Example 1 was obtained. The trade names of the ingredients used are as follows:

LAROFLEX MP-45: vinyl chloride-vinyl isobutyl ether copolymer made by BASF A.G., in Germany PLIOLITE S-5B: styrene-butadiene copolymer made by The Goodyear Co., in the U.S.A.

AEROZIL #200: silica powder made by Degsa A.G., in Germany.

size, which had been coated with a shop primer and an anti-corrosive paint of the vinyl tar type, in such a manner that a dry film of 100 μm in thickness was obtained. These sample panels were dried for 7 days, and immersed and left at rest in the sea off the coast of Miyajima in the Bay of Hiroshima at Hiroshima Prefecture, and examined for the adhesion of harmful aquatic animals and plants as well as the adhesion of slime. The results are shown in Table 3. The amount of adhering harmful aquatic animals and plants in the table was evaluated as the percentage (%) of area to which they adhered, and the amount of adhering slime in the table was evaluated by the following criteria:

0: no adhesion; 1: slight adhesion; 2: small adhesion; 3: moderate adhesion; 4: moderate to great adhesion; and 5: great adhesion.

TABLE 2

|  | Examples |  |  |  |  |  |  |  |  | Comparative |
|---|---|---|---|---|---|---|---|---|---|---|
|  | 1 | 2 | 3 | 4 | 5 | 6 | 7 | 8 | 9 | Example 1 |
| Compound (1) | 30 |  |  |  | 30 |  |  |  |  |  |
| Compound (16) |  | 30 |  |  |  |  |  |  |  |  |
| Compound (4) |  |  | 30 |  |  |  |  |  |  |  |
| Compound (8) |  |  |  | 30 |  |  |  |  |  |  |
| Compound (57) |  |  |  |  |  | 30 |  |  |  |  |
| Compound (67) |  |  |  |  |  |  | 30 |  |  |  |
| Compound (72) |  |  |  |  |  |  |  | 30 |  |  |
| Compound (80) |  |  |  |  |  |  |  |  | 30 |  |
| LAROFLEX MP-45 | 10 | 10 | 10 | 10 |  | 10 | 10 | 10 | 10 | 10 |
| PLIOLITE S-5B |  |  |  |  | 10 |  |  |  |  |  |
| Copper rhodanide |  |  |  |  |  |  |  |  |  | 30 |
| Red iron oxide | 5 | 5 | 5 | 5 | 5 | 5 | 5 | 5 | 5 | 5 |
| Zinc oxide | 5 | 5 | 5 | 5 | 5 | 5 | 5 | 5 | 5 | 5 |
| AEROZIL #200 | 1 | 1 | 1 | 1 | 1 | 1 | 1 | 1 | 1 | 1 |
| Chlorinated paraffin | 2 | 2 | 2 | 2 | 2 | 2 | 2 | 2 | 2 | 2 |
| Rosin | 10 | 10 | 10 | 10 | 10 | 10 | 10 | 10 | 10 | 10 |
| Xylene | 32 | 32 | 32 | 32 | 32 | 32 | 32 | 32 | 32 | 32 |
| Methyl isobutyl ketone | 5 | 5 | 5 | 5 | 5 | 5 | 5 | 5 | 5 | 5 |
| Total | 100 | 100 | 100 | 100 | 100 | 100 | 100 | 100 | 100 | 100 |

Test Example 1

Each of the coatings obtained in Examples 1–9 and Comparative Example 1 was applied by means of an air spray to a sandblasted steel panel of 300×100×3.2 mm in

TABLE 3

| Immersion period Adhering objects | 6 months | | 12 months | | 18 months | |
|---|---|---|---|---|---|---|
| | Slime | Harmful aquatic animals and plants | Slime | Harmful aquatic animals and plants | Slime | Harmful aquatic animals and plants |
| Example 1 | 0 | 0 | 1 | 0 | 2 | 0 |
| Example 2 | 1 | 0 | 2 | 5 | 2 | 5 |
| Example 3 | 2 | 0 | 2 | 5 | 3 | 15 |
| Example 4 | 0 | 0 | 1 | 5 | 1 | 10 |
| Example 5 | 1 | 0 | 1 | 0 | 2 | 0 |
| Example 6 | 2 | 0 | 2 | 10 | 3 | 30 |
| Example 7 | 1 | 0 | 2 | 5 | 2 | 15 |
| Example 8 | 0 | 0 | 1 | 0 | 1 | 5 |
| Example 9 | 1 | 0 | 1 | 5 | 2 | 5 |
| Comparative Example 1 | 5 | 10 | 5 | 60 | 5 | 100 |

Examples 10–18 and Comparative Examples 2–4

Various compositions containing the ingredients as shown in Table 4 were obtained in the same manner as employed in Examples 1–9. For comparison, various compositions containing the ingredients as shown in Table 5 were obtained in the same manner.

TABLE 4

| | Examples | | | | | | | | |
|---|---|---|---|---|---|---|---|---|---|
| | 10 | 11 | 12 | 13 | 14 | 15 | 16 | 17 | 18 |
| Compound (1) | 5 | | | | | | | | |
| Compound (16) | | 5 | | | | | | | |
| Compound (4) | | | 5 | | | | | | |
| Compound (8) | | | | 5 | 5 | | | | |
| Compound (57) | | | | | | 5 | | | |
| Compound (67) | | | | | | | 5 | | |
| Compound (72) | | | | | | | | 5 | |
| Compound (80) | | | | | | | | | 5 |
| LAROFLEX MP-45 | 10 | | 10 | 10 | | 10 | 10 | 10 | 10 |
| PLIOLITE S-5B | | 10 | | | 10 | | | | |
| Cuprous oxide | 30 | 30 | 20 | 20 | 20 | 30 | 30 | 30 | 30 |
| Zinc dimethyldithiocarbamate | | | 5 | | | | | | |
| 2,4,5,6-Tetrachloroisophthalonitrile | | | | 5 | | | | | |
| N,N-dimethyl-N'-(3,4-dichlorophenyl)urea | | | | | 5 | | | | |
| Red iron oxide | 5 | 5 | 5 | 5 | 5 | 5 | 5 | 5 | 5 |
| Zinc oxide | 5 | 5 | 5 | 5 | 5 | 5 | 5 | 5 | 5 |
| AEROZIL #200 | 1 | 1 | 1 | 1 | 1 | 1 | 1 | 1 | 1 |
| Chlorinated paraffin | 2 | 2 | 2 | 2 | 2 | 2 | 2 | 2 | 2 |
| Rosin | 10 | 10 | 10 | 10 | 10 | 10 | 10 | 10 | 10 |
| Xylene | 27 | 27 | 32 | 32 | 32 | 27 | 27 | 27 | 27 |
| Methyl isobutyl ketone | 5 | 5 | 5 | 5 | 5 | 5 | 5 | 5 | 5 |
| TOTAL | 100 | 100 | 100 | 100 | 100 | 100 | 100 | 100 | 100 |

TABLE 5

| | Comparative Examples | | |
|---|---|---|---|
| | 2 | 3 | 4 |
| LAROFLEX MP-45 | 10 | | |
| PLIOLITE S-5B | | 10 | 10 |
| Cuprous oxide | 30 | 30 | |
| copper rhodanide | | | 20 |
| Zinc dimethyldithiocarbamate | | | 10 |
| Red iron oxide | 5 | 5 | 5 |
| Zinc oxide | 5 | 5 | 5 |
| AEROZIL #200 | 1 | 1 | 1 |
| Chlorinated paraffin | 2 | 2 | 2 |

TABLE 5-continued

| | Comparative Examples | | |
|---|---|---|---|
| | 2 | 3 | 4 |
| Rosin | 10 | 10 | 10 |
| Xylene | 32 | 32 | 32 |
| Methyl isobutyl ketone | 5 | 5 | 5 |
| Total | 100 | 100 | 100 |

Test Example 2

The compositions obtained in Examples 10–18 and Comparative Examples 1–4 were examined in the same method as used in Test Example 1. The results are shown in Table 6.

TABLE 6

| Immersion period Adhering objects | 6 months | | 12 months | | 18 months | |
|---|---|---|---|---|---|---|
| | Slime | Harmful aquatic animals and plants | Slime | Harmful aquatic animals and plants | Slime | Harmful aquatic animals and plants |
| Example 10 | 1 | 0 | 1 | 0 | 2 | 0 |
| Example 11 | 1 | 0 | 1 | 0 | 2 | 0 |
| Example 12 | 2 | 0 | 3 | 0 | 3 | 5 |
| Example 13 | 1 | 0 | 2 | 0 | 2 | 0 |
| Example 14 | 0 | 0 | 1 | 0 | 2 | 0 |
| Example 15 | 2 | 0 | 3 | 0 | 3 | 10 |
| Example 16 | 1 | 0 | 2 | 0 | 2 | 0 |
| Example 17 | 0 | 0 | — | 1 | 0 | 2 | 0 |
| Example 18 | 1 | 0 | 1 | 0 | — | 2 | 0 |
| Comp. Ex. 1 | 5 | 10 | 5 | 60 | 5 | 100 |
| Comp. Ex. 2 | 5 | 0 | 5 | 10 | 5 | 30 |
| Comp. Ex. 3 | 5 | 0 | 5 | 10 | 5 | 30 |
| Comp. Ex. 4 | 3 | 0 | 5 | 30 | 5 | 60 |

Test Examples 3

The compositions obtained in Examples 1–4, 10–13 and Comparative Examples 2–4 were used for the test in which they were actually applied in a patch on to the bottoms of small fishing boats working in three sea areas of Nagasaki Prefecture, Hiroshima Prefecture and Niigata Prefecture. After the lapse of 6 months, the adhesion of harmful aquatic animals and plants as well as the adhesion of slime were evaluated in the same manner as described in Test Example 1. The results are shown in Table 7. The symbol "-" in the table refers to no execution of the test.

TABLE 7

| Immersion place Adhering objects | Nagasaki | | Hiroshima | | Niigata | |
|---|---|---|---|---|---|---|
| | Slime | Harmful aquatic animals and plants | Slime | Harmful aquatic animals and plants | Slime | Harmful aquatic animals and plants |
| Example 1 | — | — | 0 | 0 | 0 | 0 |
| Example 2 | — | — | 0 | 0 | 0 | 0 |
| Example 3 | — | — | 1 | 0 | 0 | 0 |
| Example 4 | — | — | 0 | 0 | 0 | 0 |
| Example 10 | 0 | 0 | 0 | 0 | — | — |
| Example 11 | 0 | 0 | 1 | 0 | — | — |
| Example 12 | 1 | 0 | 2 | 0 | — | — |
| Example 13 | 0 | 0 | 0 | 0 | — | — |
| Comp. Ex. 2 | 5 | 0 | 5 | 0 | 5 | 0 |
| Comp. Ex. 4 | — | — | 5 | 10 | 4 | 5 |

As described above, the compound (I) has an excellent effect on the prevention and inhibition of harmful aquatic organisms adhering to water-exposed articles, and such an effect can be retained for a long period of time. Accordingly, the compound (I) can find various applications in the form of a controlling agent or antifouling composition against harmful aquatic organisms.

What is claimed is:

1. An aquatic anti-fouling composition which comprises an effective anti-fouling amount of N-phenylbenzoisothiazolone derivative of the formula:

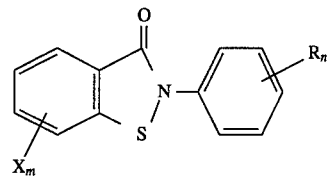

(I)

wherein R's are the same or different and are independently halogen, alkyl or alkoxy; n is an integer of 0 to 5; X's are the same or different and are independently halogen, nitro, alkyl or alkoxy; and m is an integer of 0 to 4; with the proviso that when R's are all alkyl or all alkoxy, n is an integer of 1 to 3, and when all of the R's are different, n is an integer of 2 or 3; and a copper material selected from the group consisting of a copper compound and metallic copper, present in an amount of from 0.1 to 100 parts by weight to one part of said N-phenylbenzoisothiazolone derivative.

2. An aquatic anti-fouling composition according to claim 1, wherein the R's are the same or different and are independently halogen, $C_1$–$C_{10}$ alkyl or $C_1$–$C_{10}$ alkoxy; and the m is an integer of 0.

3. An aquatic anti-fouling composition according to claim 1, wherein the n is an integer of 0 and the m is an integer of 0.

4. An aquatic anti-fouling composition according to claim 1, wherein said copper compound is a member selected from the group consisting of cuprous oxide, copper rhodanide, oxine-copper, copper naphthenate, copper glycinate, cuprous chloride and cuprous carbonate.

5. An aquatic anti-fouling composition according to claim 4, wherein the copper compound is cuprous oxide.

6. A composition according to claim 1, wherein:
said N-phenylbenzoisothiazolone derivative is present in an amount between 0.1% and 60% by weight, based on the total weight of the anti-fouling composition; and
said copper material is present in an amount of from 0.1 to 100 parts by weight to one part of said N-phenylbenzoisothiazolone derivative.

7. An anti-fouling composition against harmful aquatic organisms, which comprises an effective anti-fouling amount of an N-phenylbenzoisothiazolone derivative of the formula:

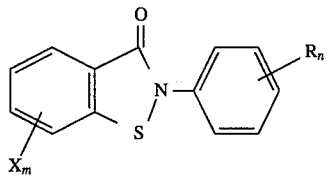

(I)

wherein R's are the same or different and are independently halogen, alkyl or alkoxy; n is an integer of 0 to 5; X's are the same or different and are independently halogen, nitro, alkyl or alkoxy; and m is an integer of 0 to 4; with the proviso that when R's are all alkyl or all alkoxy, n is an integer of 1 to 3, and when all the R's are different, n is an integer of 2 or 3, and a resin.

8. An anti-fouling composition according to claim 7, wherein the R's are the same or different and are independently halogen, $C_1$–$C_{10}$ alkyl or $C_1$–$C_{10}$ alkoxy; and the m is an integer of 0.

9. An anti-fouling composition according to claim 7, wherein the n is an integer of 0 and the m is an integer of 0.

10. An anti-fouling composition according to claim 7, which further comprises a copper material selected from the group consisting of a copper compound and metallic copper.

11. An anti-fouling composition according to claim 8, which further comprises a copper material selected from the group consisting of a copper compound and metallic copper.

12. An anti-fouling composition according to claim 9, which further comprises a copper material selected from the group consisting of a copper compound and metallic copper.

13. An anti-fouling composition according to claim 7, which further comprises metallic copper or a copper compound selected from the group consisting of cuprous oxide, copper rhodanide, oxine-copper, copper naphthenate, copper glycinate, cuprous chloride and cuprous carbonate.

14. An anti-fouling composition according to claim 8, which further comprises metallic copper or a copper compound selected from the group consisting of cuprous oxide, copper rhodanide, oxine-copper, copper naphthenate, copper glycinate, cuprous chloride and cuprous carbonate.

15. An anti-fouling composition according to claim 9, which further comprises metallic copper or a copper compound selected from the group consisting of cuprous oxide, copper rhodanide, oxine-copper, copper naphthenate, copper glycinate, cuprous chloride and cuprous carbonate copper.

16. An anti-fouling composition according to claim 13, wherein the copper compound is cuprous oxide.

17. An anti-fouling composition according to claim 14, wherein the copper compound is cuprous oxide.

18. An anti-fouling composition according to claim 15, wherein the copper compound is cuprous oxide.

19. An anti-fouling composition according to any one of claims 7–18, wherein the resin is selected from the group consisting of vinyl chloride resins, vinyl chloride-vinyl acetate copolymers, vinyl chloride-vinyl isobutyl ether copolymers, chlorinated rubber resins, chlorinated polyethylene resins, chlorinated polypropylene resins, acrylic resins, styrene-butadiene copolymers, polyester resins, epoxy resins, phenolic resins, synthetic rubbers, silicone rubbers, silicone resins, petroleum resins, oil resins, rosin ester resins, rosin soap and rosin.

20. A composition according to claim 7, wherein:
said N-phenylbenzoisothiazolone derivative is present in an amount between 0.1% and 60% by weight, based on the total weight of the anti-fouling composition; and
said resin is present in an amount between 0.1% and 80% by weight based on the total weight of the composition.

21. A composition according to claim 20, which further comprises a copper material selected from the group consisting of a copper compound and metallic copper, present in an amount of from 0.1 to 100 parts by weight to one part of said N-phenylbenzoisothiazolone derivative.

22. A method for preventing or inhibiting the adhesion of harmful aquatic organisms to a water-exposed article, which comprises applying an effective anti-fouling amount of the anti-fouling composition according to claim 7 to the water-exposed article.

23. A method according to claim 22, wherein the water-exposed article is present in the sea.

24. A method according to claim 23, wherein the water-exposed article is a marine vessel.

25. A method for preventing or inhibiting the adhesion of harmful aquatic organisms to a water-exposed article, which comprises applying an effective anti-fouling amount of an anti-fouling composition containing N-phenylbenzoisothiazolone to a water-exposed article.

26. A method for preventing or inhibiting the adhesion of harmful aquatic organisms to a water-exposed article which comprises applying an effective anti-fouling amount of an anti-fouling composition containing an N-phenylbenzoisothiazolone derivative of the general formula:

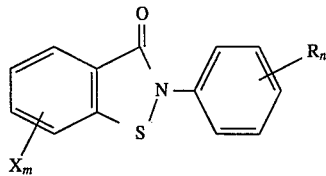

(I)

wherein R's are the same or different and are independently halogen, $C_1$–$C_{10}$ alkyl or $C_1$–$C_{10}$ alkoxy; X's are the same or different and are independently halogen, alkyl or alkoxy; n is an integer of 0 to 5; and m is an integer of 0 with the proviso that when R's are all alkyl or all alkoxy, n is an integer of 1 to 3, and when all the R's are different, n is an integer of 2 or 3, and a resin.

27. A method according to claim 26, wherein the n is an integer of 0.

* * * * *